United States Patent
Bardarov et al.

(12)

(10) Patent No.: US 6,271,034 B1
(45) Date of Patent: Aug. 7, 2001

(54) ONE STEP ALLELIC EXCHANGE IN MYCOBACTERIA USING IN VITRO GENERATED CONDITIONAL TRANSDUCING PHAGES

(75) Inventors: Stoyan S. Bardarov, Bronx; William R. Jacobs, Jr., City Island, both of NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/350,048

(22) Filed: Jul. 8, 1999

(51) Int. Cl.[7] .......................... C12N 15/74; C12N 15/63; C12N 1/00; C12N 1/15

(52) U.S. Cl. .................. 435/472; 435/477; 435/253.1; 435/243; 435/320.1

(58) Field of Search .................. 435/472, 253.1, 435/320.1, 477, 243

(56) References Cited

PUBLICATIONS

Bardarov, et al. Proceedings of the National Academy of Sciences, USA. vol. 94, pp. 10961–10966, Sep. 1997.*

Pelicic, et al. Proceedings of the National Academy of Sciences, USA vol. 94, pp. 10955–10960, Sep. 1997.*

* cited by examiner

*Primary Examiner*—David Guzo
*Assistant Examiner*—Gerald G. Leffers, Jr.
(74) *Attorney, Agent, or Firm*—Amster, Rothstein & Ebenstein

(57) ABSTRACT

The present invention provides a method for high frequency of allelic exchange in the slow-growing mycobacteria using in vitro generated specialized transducing mycobacteriophages, as well as the recombinant slow-growing mycobacteria generated using the disclosed method. A transducing mycobacteriophage of the present invention comprises a conditional mycobacteriophage containing an *E. coli* bacteriophage lambda cosmid inserted into a non-essential region of the mycobacteriophage, said cosmid containing a mutated DNA substrate which is homologous to a wildtype nucleic acid sequence of a slow-growing mycobacterium. When slow-growing mycobacteria infected with the conditional transducing phage are cultured under conditions wherein the conditional transducing phage does not replicate, the mutated DNA substrate is incorporated into the chromosomal DNA of the slow-growing mycobacteria by homologous recombination, thereby generating the recombinant slow-growing mycobacteria of the present invention. The disclosed method may be used to produce mycobacterial auxotrophs, including leucine and lysine auxotrophs.

18 Claims, 4 Drawing Sheets

A

Complete                    Minimal

B

PCR

ONE STEP ALLELIC EXCHANGE IN MYCOBACTERIA USING IN VITRO GENERATED CONDITIONAL TRANSDUCING PHAGES

Statement of Government Interest

This invention was made with government support under NIH Grant No. AI-26170. As such, the United States government has certain rights in this invention.

BACKGROUND OF THE INVENTION

In April 1993, tuberculosis was declared a global health emergency—the first such designation in the history of the World Health Organization. The distinction is regrettably justified because tuberculosis remains one of the largest causes of disease and death in the world (37), due in part to the increased susceptibility of HIV infected individuals and the ominous emergence of multi-drug resistant strains in both industrialized and developing countries. Effective new tuberculosis control and prevention strategies will require additional knowledge of the causative agent and its interaction with the human host.

In this regard, the determination of the genomic sequence of Mycobacterium tuberculosis (7) has provided many new opportunities for studying tuberculosis pathogenesis. Many of the genes in the genome of M. tuberculosis have no known function. A first step in establishing a function of an unknown gene lies in the generation of a mutation in that gene and characterization of the resulting mutant strain. Studying the behavior of these mutants in model systems of tuberculosis could reveal the mechanisms by which M. tuberculosis multiplies within the host cells and resists the immune effector functions of the host.

The availability of the M. tuberculosis genome sequences and the development of successful transformation protocols for the slow growing mycobacteria (32, 34) make the engineering of specific mutations readily achievable, but the introduction of these mutated alleles into their homologous sites in the chromosome, i.e. allelic exchange, has been notoriously difficult in this organism. Slow growing mycobacteria such as M. bovis BCG and M. tuberculosis can integrate exogenous DNA into their chromosome by both illegitimate and homologous recombination (13, 16). In recent years, numerous successful gene disruptions in various mycobacterial species were reported by using short (1, 13, 28) or long linear DNA fragments (2) as homologous DNA substrates. A "suicidal" vector approach, using recombinant plasmids unable to replicate in mycobacteria, was also extensively used to achieve allelic exchange in both fast- and slow-growing mycobacteria (5, 14) (22) (23) (24, 25, 31). Unfortunately, it is very difficult to estimate the real frequency of the allelic exchange events in these experiments due to the low number of transformants obtained, especially when using slow-growing mycobacteria. This led to the general conclusion that homologous recombination in the slow-growing mycobacteria is inefficient (16).

A two-step selection method using a selectable and counter-selectable marker positioned on either replicating or non-replicating plasmids has been successfully used in M. smegmatis (14, 24). Further, use of a conditionally replicating temperature sensitive plasmid as a delivery vector has greatly improved reproducibility of the allelic exchange in the slow growing mycobacteria (23).

However, the natural mechanisms of exchange of genetic information, such as conjugation or transduction, would be an alternative strategy to introduce homologous DNA into mycobacteria with high efficiency. Although conjugation has been described for M. smegmatis (17, 20, 33), it has not been demonstrated in the slow-growing mycobacteria. Similarly, transduction has been reported for M. smegmatis (26), but not for BCG or M. tuberculosis.

Because the creation of mutants in M. tuberculosis and BCG is of essential importance in the analysis of gene function, it is desirable to develop effective means and methods for allelic exchange for M. tuberculosis, BCG and other slow-growing mycobacteria. Methods for efficient allelic exchange would facilitate the definition of wildtype and mutant genes of M. tuberculosis and BCG mycobacteria, and thereby provide the necessary tools for understanding the mechanisms by which these mycobacteria survive and replicate. In addition, it would further the development of vaccines and new drugs effective in the treatment of infection caused by M. tuberculosis, BCG, and other mycobacteria.

SUMMARY OF THE INVENTION

The present invention describes a novel one-step method for achieving high frequency allelic exchange in the fast- and slow-growing mycobacteria using in vitro generated conditional transducing phages. The present invention provides a method for producing a recombinant mutant mycobacterium, including a recombinant mutant slow-growing mycobacterium, comprising infecting a mycobacterium with a conditional transducing phage where the conditional transducing phage comprises a mutated DNA substrate for allelic exchange with a homologous wildtype nucleic acid sequence of the mycobacterium. The infected mycobacterium is cultured under conditions wherein the conditional transducing phage does not replicate. The mutated DNA substrate is incorporated into the chromosome of the mycobacterium by homologous recombination, thereby generating a recombinant mutant mycobacterium having the mycobacterial DNA substrate in lieu of the homologous wildtype nucleic acid sequence of the mycobacterium.

The present invention further provides a conditional transducing phage, comprising a conditional mycobacteriophage comprising an E. coli bacteriophage lambda cosmid inserted into a non-essential region of the mycobacteriophage, wherein said cosmid further comprises a mutated DNA substrate which is homologous to a wildtype nucleic acid sequence of a mycobacterium.

Also provided is a recombinant mutant mycobacterium, including recombinant mutants or auxotrophs resulting from the selective disruption of one or more genes in the biosynthetic pathway of a nutrient, structural component or amino acid, where the recombinant mutant mycobacterium is produced by a method comprising infecting a mycobacterium with the conditional transducing phage of the present invention, and culturing the infected mycobacterium under such conditions wherein the conditional transducing phage does not replicate and the mutated DNA substrate carried by the transducing phage is incorporated into the chromosome of the mycobacterium by homologous recombination. The present invention further provides for recombinant mutant slow- and fast-growing mycobacteria that are auxotrophic for lysine, as well as recombinant mutant slow-growing mycobacteria that are auxotrophic for leucine. Additional objects of the present invention will be apparent from the description which follows.

DETAILED DESCRIPTION OF THE INVENTION

Figure 1:
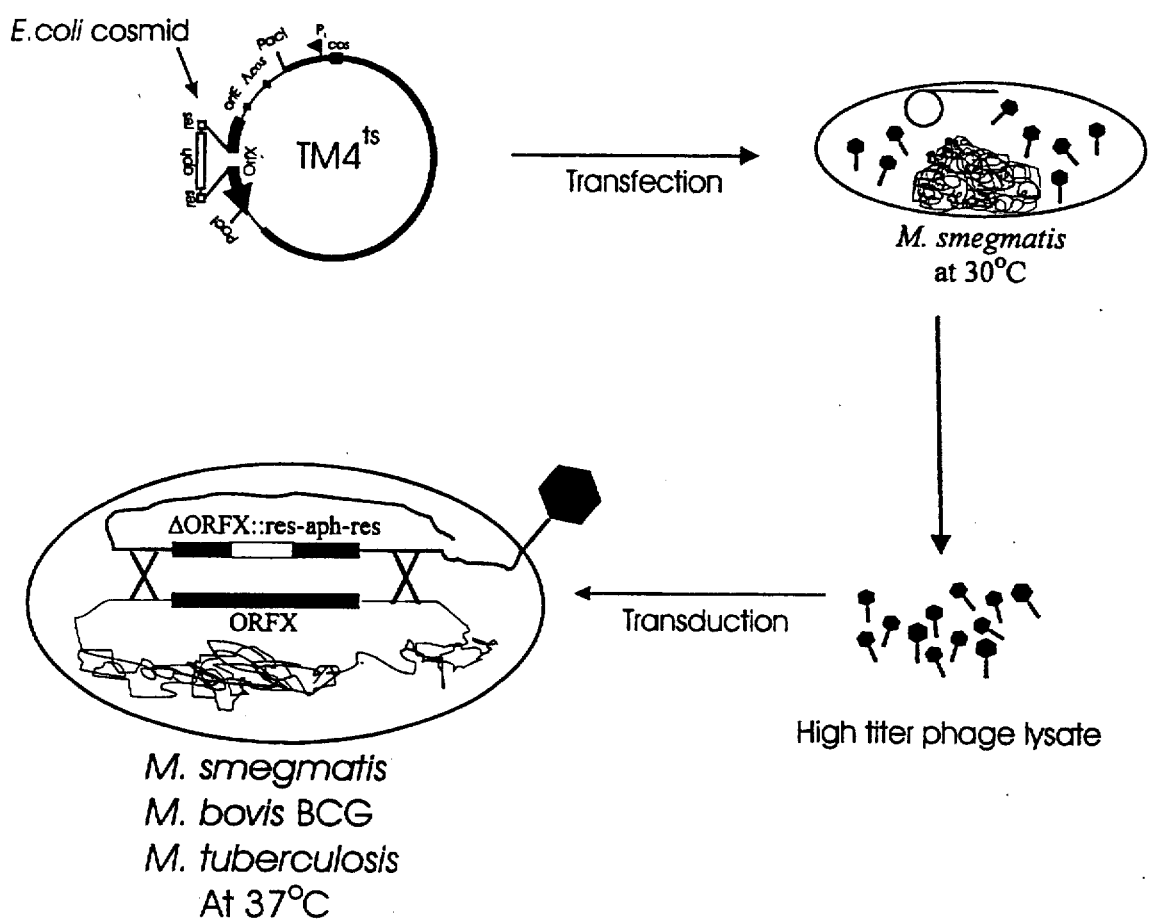
FIG. 1 depicts a schematic of one step gene replacement in mycobacteria using in vitro constructed specialized conditional transducing phages. The desired mycobacterial gene is amplified using PCR and cloned into E. coli plasmid (pBluescript®). A deletion is generated by restriction enzyme digestion or long range inverse PCR and marked with a res-aph-res or res-hyg-res gene cassette. The recombination substrate is introduced into the conditionally replicating TM4ts phage (designated as phAE87, deposited with the American Type Culture Collection (ATCC) under Accession No. 209306) to produce a specialized conditional transducing phage. High titer lysates of this recombinant phage are obtained by propagating in M. smegmatis at 30° C. The lysates are mixed with the host cells at an MOI of 10, incubated at 37° C. to allow absorption of the phage, after which cells are plated on selective media at 37° C. Antibiotic resistant transductants are analyzed for auxotrophy by plating on complete and minimal media and for the presence of allelic exchange by PCR or Southern blotting.

The present invention provides a novel method for yielding high frequency allelic exchange in fast- and slow-growing mycobacteria using in vitro generated specialized conditional transducing mycobacteriophages. The method of the present invention is particularly suited for generating mutants via allelic exchange in Mycobacterium tuberculosis complex organisms, preferably strains of M. tuberculosis, M. bovis and Bacille-Calmette-Geurin (BCG), which are slow-growing mycobacteria, as well as in other slow growing mycobacteria, in addition to nontuberculosis fast-growing mycobacteria commonly encountered in biological samples isolated from human subjects, e.g., M. avium-intracellulare, M.kansasii, M. xenopi, M. scrofulaceum, M. simiae, M. szulgai, M. gordonae, M. gastri, M. smegmatis, and M. chelonae. As used herein, the term "mutated mycobacterium" means that the mutated mycobacterium possesses at least one mutant gene such that the expression or function of the gene is varied with respect to the non-mutated gene in the parent strain.

In the method of the present invention, a mycobacterium is infected with a conditional transducing phage comprising a mutated DNA substrate which is homologous to a wildtype nucleic acid sequence of the mycobacterium in which it is desired to introduce the mutated DNA substrate by allelic exchange. The infected mycobacteria is grown at the nonpermissive temperature (i.e., under conditions wherein the conditional transducing phage does not replicate). The phage DNA thus enters the mycobacterium, but without lysis of the infected mycobacterium. In this way, the mutated DNA substrate for allelic exchange can become integrated into the mycobacterial chromosome via homologous recombination with the homologous mycobacterial nucleic acid sequence, resulting in a replacement of the wildtype nucleic acid sequence of the mycobacterium with the nucleotide sequence of the mutated DNA substrate. The method of the invention may be used to produce recombinant mutant fast-growing mycobacteria, including recombinant mutant strains of M. smegmatis or M. avium, but is preferably used to produce recombinant mutant strains of slow-growing mycobacteria, and more preferably, recombinant mutants of M. tuberculosis, M. bovis BCG or M. leprae.

The vector of the present invention which introduces the mutated DNA substrate for allelic exchange into a mycobacterium is a specialized conditional transducing phage. "Conditional" phages as used herein are those which replicate only under certain conditions, such as a specific temperature. In a preferred embodiment of the invention, the conditional transducing phage is a TM4 phage which replicates at 30° C., but fail to replicate and lyse its host cell at 37° C. This conditional transducing phage is produced by inserting the mutated DNA substrate for allelic exchange into a cosmid which is in turn inserted into a non-essential region of the genome of a TM4 mycobacteriophage. The term "inserted" as used herein means the ligation of the foreign DNA fragment and vector DNA by techniques such as the annealing of compatible cohesive ends generated by restriction endonuclease digestion or by use of blunt end ligation techniques. Other methods of ligating DNA molecules will be apparent to one skilled in the art. In a preferred embodiment of the invention, the mutated DNA substrate for allelic exchange is inserted into the E. coli bacteriophage lambda cosmid of the conditional shuttle phasmid designated as phAE87, said phasmid being deposited under the terms of the Budapest Treaty on Sep. 26, 1997 with the American Type Culture Collection (ATCC), Rockville, Md. and assigned Accession No. 209306. phAE87 is constructed according to the methods disclosed in co-pending U.S. patent application Ser. No. 08/938,059, now U.S. Pat. No. 5,972,700, filed Sep. 26, 1994, entitled TM4 CONDITIONAL SHUTTLE PHASMIDS AND USES THEREOF, the contents of which are hereby expressly incorporated by reference.

The DNA substrate for allelic exchange may be of any origin, but is preferably from a mycobacterium. In a preferred embodiment of the invention, the mutated DNA substrate for allelic exchange is from a mycobacterium and is homologous to a wildtype nucleic acid sequence of the mycobacterium in which it is desired to introduce the mutated DNA substrate in lieu of the wildtype nucleic acid sequence.

The DNA substrate for allelic exchange contains the mutation of interest, which through allelic exchange, is introduced into the homologous region of the mycobacterium nucleic acid. As used herein, "mutated DNA substrate" refers to the nucleotide sequence for at least one allele that has been modified by addition, substitution or deletion of at least one nucleotide. In a preferred embodiment of the invention, the mutated DNA substrate comprises a deletion mutation of the wildtype nucleic acid sequence. Mutations, including but not limited to deletion, substitution, or insertion mutations, may be generated by any number of methods known in the art, including but not limited to treatment with restriction endonucleases, inverse PCR and subcloning techniques. The wildtype nucleic acid sequence may encode a protein or polypeptide, and in a preferred embodiment of the invention encodes an enzyme essential in the biosynthetic pathway of a nutrient, structural or cell wall component of the mycobacterium, or an amino acid, such as lysine or leucine. It is also within the confines of the present invention that the wildtype nucleic acid of the mycobacterium may comprise an operon or cluster of alleles encoding a number of proteins or polypeptides, or one or more promoters, enhancers or regulators that are involved in the expression and translation of mycobacterial proteins and polypeptides. In a preferred embodiment of the invention, the wildtype nucleic acid comprises the lysA gene or the leu CD genes.

In addition to the mutated DNA substrate for allelic exchange, a selectable marker gene, including but not limited to a gene which confers antibiotic resistance, may be ligated to the DNA substrate and the resultant molecule ligated into phAE87 or equivalent phasmid using standard procedures. Selectable marker genes which may be included in the DNA substrate are well known in the art and include but are not limited to genes encoding resistance to antibiotics such as kanamycin, ampicillin, viomycin, thiostrepton, hygromycin or bleomycin.

The resulting ligated DNA comprising phasmid DNA, mutated DNA substrate and/or selectable marker DNA is then packaged into bacteriophage lambda heads using a commercially available in vitro packaging mix. E. coli is subsequently transduced with the phage mixture containing the ligated DNA, and transductants are isolated by virtue of their ability to grow in medium containing the antibiotic corresponding to the selectable marker gene on the cosmid. The resulting conditional phasmids are isolated and introduced into any infectible mycobacterium which is able to replicate at the permissive temperature, e.g., M. smegmatis at 30° C.

The resulting plaques which contain conditional transducing phages comprising the mutated DNA substrate may then be used to infect mycobacteria of interest, e.g., M. tuberculosis and BCG. Mycobacteria that have undergone allelic exchange can be detected by virtue of their survival and growth on the appropriate selective medium, as well as by screening for auxotrophy resulting from disruption of the wildtype allele in the mycobacteria, where appropriate, or by using PCR analysis, Southern blot analysis or other suitable methods known in the art.

The method of the present invention may be used to generate numerous strains of auxotrophic recombinant mutant mycobacteria that are auxotrophic for a particular nutrient or nutrients by reason of the substitution via allelic exchange of a wildtype nucleic acid sequence of a mycobacterium with a mutated DNA substrate. As used herein, the term "auxotrophic recombinant mutant mycobacterium" is defined as a mycobacterium having a nutritional mutation whereby the nutritional requirements of the mycobacterium are altered. For example, some auxotrophic mutants are unable to synthesize amino acids, or may require specific amino acids that are not needed by the parental or prototrophic strain. Specific auxotrophic recombinant mutant mycobacteria of the present invention include slow-growing mycobacteria which are auxotrophic for leucine or lysine. Preferably, the auxotrophic recombinant mutant mycobacteria are strains of M. bovis BCG or M. tuberculosis, but the invention is not limited to these species of mycobacteria. In a specific embodiment of the invention, the auxotrophic recombinant mutant mycobacteria that is auxotrophic for lysine comprises a mutation of the lysA gene, while the auxotrophic recombinant mutant mycobacteria that is auxotrophic for leucine comprises a mutation of the leuCD gene.

The present invention provides a vaccine comprising an auxotrophic recombinant mutant mycobacterium that is auxotrophic for leucine and/or lysine, and a method of treating or preventing tuberculosis in a subject in need of such treatment or prevention using the vaccine. In this regard, the vaccine containing the recombinant mutant mycobacteria of the present invention may be administered in conjunction with a suitable physiologically acceptable carrier. Mineral oil, alum, synthetic polymers, etc., are representative examples of suitable carriers. Vehicles for vaccines and therapeutic agents are well within the skill of one skilled in the art. The selection of a suitable vaccine is also dependent upon the manner in which the vaccine or therapeutic agent is to be administered. The vaccine or therapeutic agent may be in the form of an injectable dose and may be administered intramuscularly, intravenously, orally, intradermally, or by subcutaneous administration.

Further, the recombinant mutant mycobacterium of the present invention that is auxotrophic for lysine may be used in the construction of DAP auxotrophs (peptidoglycan mutants).

The present invention is described in the following Experimental Details Section which is set forth to aid in the understanding of the invention, and should not be construed to limit in any way the scope of the invention as defined in the claims which follow thereafter.

Experimental Details Section

A) Experimental Methods

Bacterial strains, media and culture methods: The bacterial strains used in this study are listed in Table 1. The E. coli strains were grown in LB (Luria-Bertani) broth or on LB agar (DIFCO) for the amplification of recombinant clones, plasmid isolation, and transformation, and in 1% tryptone, 0.5% yeast extract, 0.5% NaCl, 0.2% maltose (TYM broth) for transduction with λ-packaged cosmids. For the preparation of electro-competent cells M. smegmatis mc$^2$ 155 was grown in LB broth containing 0.5% (wt/vol) Tween 80 (LBT) (22). When required, the following antibiotics were used at the specified concentrations: carbenicillin (50 μg/ml), kanamycin (25 μg/ml) and hygromycin B (50 μg/ml for E. coli and 150 μg/ml for M. smegmatis). Hygromycin B was purchased from Boehringer Mannheim (50 mg/ml in phosphate buffered saline), all other antibiotics were purchased from Sigma Chemical. Mycobacterial strains (except for *M. smegmatis*) were grown in basal Middlebrook 7H9 broth (DIFCO) supplemented with 1× ADS ( 0.5% bovine serum albumin, fraction V (Boehringer, Manheim), 0.2% glucose and 0.085% NaCl), 0.2% glycerol, and 0.1% Tween-80, (M-ADS-TW broth) (11). Complete media consists of M-ADS-TW supplemented with individual L-amino acids (Sigma Chemical) at a final concentration of 80 µg/ml. For the transduction experiments cultures of the BCG strains were prepared by inoculating 10 ml M-ADC-TW broth with 1 ml frozen stock into 30 ml plastic culture bottles and incubated at 37° C. in an incubator-shaker (100 rpm). Larger cultures were prepared by inoculating 100 ml of M-ADS-TW broth with 1 ml of a seven day old culture into a 490-cm$^2$ roller bottle (Corning, Coming, N.Y.) and incubating at 37° C. on a roller at 8 rpm. For propagation of mycobacteriophages in *M. smegmatis* mc$^2$155 Tryptic Soy Agar (Difco), supplemented with 0.4% glycerol and 2 mM CaCl$_2$ was used as a bottom agar, and 0.6% agar in water supplemented with 2 mM CaCl$_2$ was used as a top agar. High titer suspensions of mycobacteriophage were routinely prepared from phage propagated in *M. smegmatis* grown on this solid media at 30° C. Phage lysates were stored in MP-buffer (50 mM Tris.HCl pH 7.6, 150 mM NaCl, 10 mM MgCl$_2$ and 2 mM CaCl$_2$). Absorption of the phages was performed for 30 min at 37° C. Outgrowth of the infected cells was performed by transferring the phage-cell mixture in a roller bottle containing 50 ml of complete M-ADS-TW pre-warmed to 37° C.

DNA Purification: Plasmids and phasmids used in this study are listed in Table 2. DNA manipulations were done essentially as previously described (30). Plasmid and phasmid constructions were performed in *E. coli* DH5α or *E. coli* HB101 and DNA purified by an alkaline lysis mini-prep method. Larger amounts plasmid or phasmid DNA were purified by using Qiagen (Chatsworth, Calif.) kit as recommended by the manufacturer. DNA fragments were analyzed by agarose gel electrophoresis and DNA fragments for the construction of recombinant plasmids were purified by absorption to glass beads (GeneClean, Bio 101, Vista, Calif.). High-molecular weight chromosomal DNA from *M. smegmatis* or *M. bovis* BCG was purified as described previously (2) from bacteria grown in 50 ml cultures with glycine added to final concentration of 1% 24 hours prior cell harvest. Phage DNA from mycobacteriophages was purified as previously described (11) with slight modifications. High titer phage lysates (30 ml) were layered onto 5 ml cushion of 50% glycerol in MP buffer in a 35 ml nitrocellulose centrifuge tube (Beckman, Palo Alto, Calif.) and centrifuged at 25,000 rpm for 2 hours in SW27 rotor at 15° C. Phage pellets were resuspended in 500 µl MP buffer to which 25 µl (0.05% vol/vol) of STEP lysis solution (0.4 M EDTA.Na$_2$ 1% SDS, 50 mM Tris.HCl pH 8.0, Proteinase K 500 µg/ml,) was added and the suspension was incubated for 30 min at 56° C. Following extraction with phenol:chlorophorm (1:1) and chloroform:isoamyl alcohol (24:1), phage DNA was precipitated by the addition of 2 vol of 100% ethanol, washed in 70% ethanol, air-dried and resuspended at a concentration approximately 200 µg/ml in TE buffer (10 mM Tris.HCl pH 8.0, 1 mM EDTANa$_2$,).

Construction of specialized transducing mycobacteriophages: Plasmid pYUB665 was used as a source for the *M. tuberculosis* ΔlysA5:res-aph-res gene (21) . A specialized res-aph-res gene cassette marks the deletion in the lysA gene. The specialized cassette has an aph gene flanked by two γδ resolvase sites from the *E. coli* transposon γδ (Tn1000) (4, 9, 27). The presence of the resolvase sites makes it possible to excise the antibiotic marker by transiently expressing the resolvase (tnpR) gene after the cassette has been inserted into the mycobacterial chromosome. A 4198 bp BclI-AscI fragment from pYUB665 containing the ΔlysA5:res-aph-res gene flanked by about 1 kb DNA sequence each side was cloned by blunt end ligation into a BspHI digested cosmid pYUB572 to generate pYUB586.

To isolate the leuCD operon primers Pleu1 (5'-TGAACACCGCCTTTGGCAAT-3') (SEQ. ID NO:1) and Pleu2 (5'-GCCTTACGCACCGATGCCTT-3') (SEQ. ID NO:2) were designed using the *M. tuberculosis* genome sequence data base (7) to amplify 3342 bp DNA fragment from *M. bovis* BCG (strain Pasteur) chromosomal DNA containing the leuC and leuD genes symmetrically flanked by about 0.6 kb homologous DNA sequence each side. This PCR product was cloned into the unique EcoRV site of pBluescript I$^+$KS plasmid by blunt end ligation. A deletion of 944 bp was generated by cleavage with MluI and SphI and marked with the res-aph res gene cassette introduced by blunt end ligation. The resulting plasmid, pYUB595, was digested with PstI and HindIII to produce a 3342 bp DNA fragment containing ΔleuCD6:res-aph-res. This fragment was cloned into BspHI digested pYUB572 by blunt end ligation to generate the cosmid pYUB597.

The *M. smegmatis* ΔlysA4:res-hyg-res phasmid was constructed from the plasmid pYUB617 (21). This plasmid contains the ΔlysA4 deletion allele, the res-hyg-res cassette was introduced into the unique SnaB1 site at the deletion point in the ΔlysA4 allele, yielding the plasmid pYUB619. A 4130 BamHI-NotI fragment containing the ΔlysA4:res-hyg-res allele was cloned into BspHI digested pYUB572 by blunt end ligation to generate two cosmids, pYUB854 and pYUB855, differing by the orientation of the ΔlysA4:res-hpt-res with respect to the BamH1 site in the cosmid.

Construction of specialized transducing mycobacteriophages: Concatemers of phAE87 were prepared by self ligation of purified phage DNA which were then digested with PacI. To generate the specialized transducing phages phAE128 and phAE134, PacI digested cosmids pYUB586 and pYUB597 were used to replace the pYUB328 cosmid in phAE87 in an in-vitro λ-packaging reaction (GIGAPackII, Stratagene). After transducing *E. coli* HB101 and plating the transductants on selective media containing kanamycin, phasmid DNA was prepared from the pooled antibiotic resistant transductants and electroporated into *M. smegmatis* mc$^2$155. In a similar fashion, transducing phages phAE143 and phAE144 were constructed using PacI digested cosmids pYUB854 and pYUB855. All transducing phages were plaque purified and tested for temperature sensitive phenotype. The presence of the homologous DNA substrate in the recombinant phages was confirmed by Southern blot analysis. Plaque purified phages were amplified to a high titer in *M. smegmatis* mc$^2$155 at 30° C.

Transduction protocol: *M. smegmatis* mc$^2$155 was grown in LBT to an OD at A$_{600}$ of 1.0 (6×10$^8$ cfu/ml). *M. bovis* BCG strains were grown in M-ADS-TW to an OD at A$_{600}$ 0.8–1.0) . Ten milliliters of the culture was centrifuged and resuspended in 10 ml washing media (7H9-ADS-10% glycerol) and incubated as standing cultures at 37° C. for at least 24 hours. This incubation is necessary to remove traces of the Tween-80 detergent which can inhibit phage infection. After this incubation period the cells are washed again and resuspended in 1.0 ml absorption media (7H9-ADS-5%Glycerol) pre-warmed at 37° C., and mixed with specialized transducing phage at a multiplicity of infection (MOI) of 10. The cell-phage mixture is incubated at the non-permissive temperature (37° C.) for 30 min (*M. smegmatis*) or 3 hours (BCG), after which the mixture is inoculated into 50 ml LBT (*M. smegmatis*) or M-ADS-TW (BCG strains) pre-warmed at 37° C. Outgrowth of the cultures is performed for 30 min (*M. smegmatis*) or 24 hours (BCG) at 37° C. Cells are pelleted by centrifugation, resuspended in PBS-TW (0.5% Tween-80 in phosphate buffered saline) and plated on M-ADS-TW containing 25 μg/ml kanamycin and 80 μg/ml of the respective L-amino acid (L-lysine or L-leucine). Auxotroph analysis was performed by plating the transductants on complete and minimal media. Transduction frequencies were calculated by dividing the number of $Hyg^R$ or $Kan^R$ colonies obtained minus the number of spontaneous drug-resistant colonies from control cells receiving no phage by the total number of viable cells. The frequency of allelic exchange was calculated as the percentage of auxotrophs in the population of $Kan^R$ transductants.

PCR analysis and Southern blotting: PCR amplification was performed with AmpliTaq polymerase (Perkin-Elmer) under standard conditions. Primer concentrations and cycling conditions were adjusted depending on the size of the amplified product. Long range inverted PCR was performed using a hot-start technique with rTth polymerase using PCR XL-Kit (Perkin-Elmer). All PCR reactions were performed in Perkin-Elmer 9600 thermal cycler. The following diagnostic primers were used to analyze the auxotroph strains:Pv21 (5'-GAATTCCA CTGACGCAGCTC-3') (SEQ. ID NO:3) and Pv22 (5'-GCCGACCATGTTGTAACGAC-3') (SEQ. ID NO:4) for lysA; PleuCD1 (5'-GG AAGGCCGGATGACGATCT-3') (SEQ. ID NO:5) and PleuCD2 (5'-TCTTGAAC GGCA GCACCACT-3') (SEQ. ID NO:6) for leuCD. Southern blotting was done by the alkali-denaturing procedure. DNA was transferred to HyBond-N+ membrane (Amersham) by the capillary method. Hybridization and detection were done with a chemiluminescent detection system (ECL, Amersham) as recommended by the manufacturer, under high stringency conditions for the pre-hybridization and hybridization (0.1 M NaCl and 42° C.). Washes were done at 42° C. with primary wash buffer containing 6 M urea and 0.1×SSC (1×SSC is 0.15 M NaCl plus 0.015 M sodium citrate).

B) Experimental Results

Specialized transduction methodology: Conditionally replicating mycobacteriophages had proven to be a highly efficient system for generating large libraries of independent transposon mutants in *M. tuberculosis* and BCG, as they provide the means to deliver the transposon constructs to virtually every cell in the bacterial population (3). The inventors reasoned that this system could be modified to generate specialized transducing mycobacteriophages which could deliver DNA substrates for allelic exchange (FIG. 1). PhAE87 was used as a phage vector, a temperature sensitive TM4 phage which infects a broad range of mycobacterial cells. It replicates and forms clear plaques at 30° C. in *M. smegmatis*, but fails to kill the cells at 37° C. (3, 6). The PacI excisable cosmid pYUB328 in this shuttle phasmid can be easily replaced in *E. coli* with cosmids containing mycobacterial chromosomal DNA fragments engineered as substrates for gene disruption. High titer lysates of the transducing phages could then be prepared in *M. smegmatis* and used to infect the recipient cells.

Figure 2:
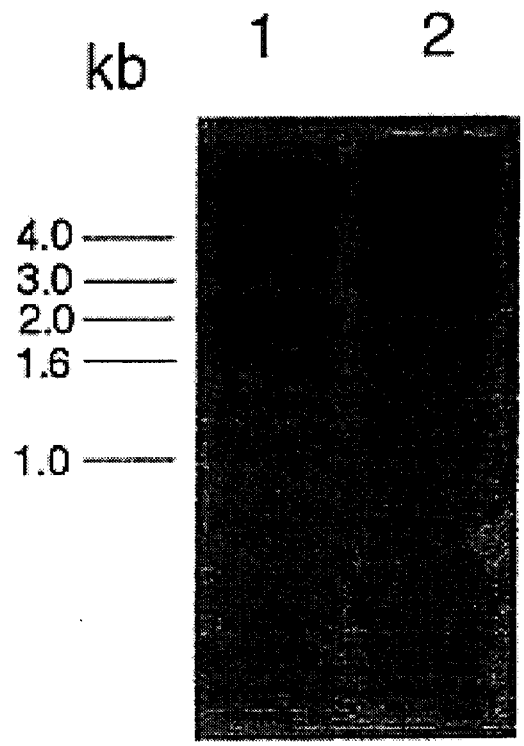
FIG. 2 shows Southern blot analysis of genomic DNA from wild type M. smegmatis $mc^2155$ (Lane 1) and M. smegmatis $mc^2$ 1494 (Lane 2) digested with PvuII and probed with a 2.3 kb EcoR1 fragment from pYUB619 encompassing the ΔlysA4:res-hyg-res allele. The wild type fragment is the expected 1.9 kb, wile the genomic DNA from the mutant has the expected 3.4 kb fragment.

Construction of lvsA auxotrophic mutant of *M. smegmatis* by specialized transduction: The inventors decided to initially test the present invention in the fast growing mycobacterium *M. smegmatis* $mc^2 155$, a surrogate host for the analysis of genes from pathogenic mycobacteria. This would allow design of a useful methodology for strain construction in this very useful genetic background. Plasmid pYUB619 (21) was digested with NotI and BamHI and the resulting 4552 bp fragment, containing ΔlysA4:res-hyg-res gene, was purified and cloned into pYUB572 cosmid to yield the cosmid pYUB854. The inventors generated two types of specialized transducing phages—phAE143 with ΔlysA4:res-hyg-res in the same transcriptional orientation with the phage transcription (8), and phAE144 with the ΔlysA allele in the opposite orientation. *M. smegmatis* cells were adsorbed with the transducing phages at MOI of 10 for 15 min and phage-cell mixtures were plated on complete medium containing hygromycin immediately or after an outgrowth time for 2 hours at 37° C. in the presence of the phage (Table 3). As shown in Table 3 a comparable number of $Hyg^R$ colonies were obtained for both incubation times. The observed transduction frequencies were in the range of $10^{-6}$ for the phage-infected cells, whereas the frequencies of $Hyg^R$ colonies for uninfected cells were routinely less than $10^{-8}$. Cell suspensions infected with phAE143, containing the hygromycin gene in the same orientation as the major phage transcript, gave rise to a lawn of cells on the hygromycin media, with large colonies on top of the lawn. This was not observed with the phasmid phAE144 which has the hygromycin gene in an opposite transcriptional orientation. It is believed that the transcriptional read trough from the phasmid into the hygromycin gene was strong enough to promote the appearance of abortive transductants on the selection media in the phAE143 experiment. When true $Hyg^R$ transductants were screened for auxotrophy, a strikingly high percentage (90% to 95%) of the transductants were lysine auxotrophs. Southern analysis confirmed allelic exchange of the ΔlysA4:res-hyg-res allele with the wild-type lysA allele (FIG. 2).

Figure 3:
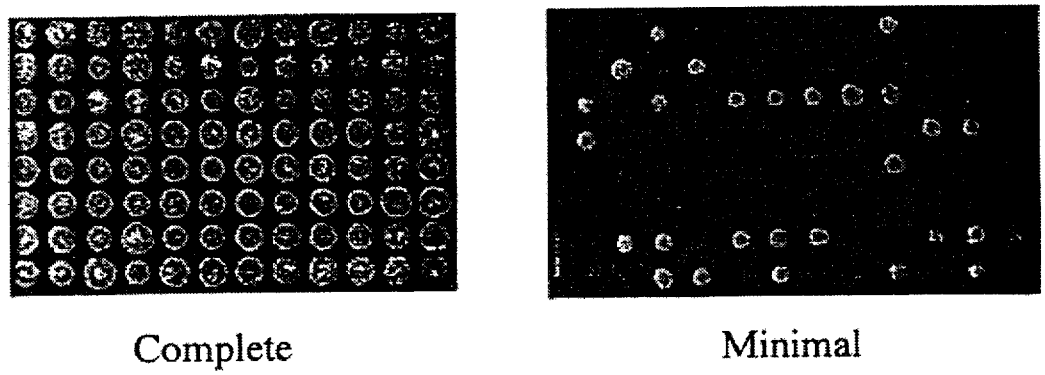
FIG. 3 is an analysis of M. bovis BCG ΔlysA5:res-aph-res lysA auxotrophic mutants obtained by specialized transduction with phAE128. Panel A depicts a 96-well plate auxotroph screen of BCG Pasteur transductants plated on minimal and complete medium. Panel B illustrates the results of PCR analysis of 12 arbitrary chosen kanamycin resistant BCG Pasteur transductants using primers Pv21 and Pv22 (Lanes 5 to 16). Negative controls include a plasmid pYUB665 bearing the wild type lysA gene (Lane 2), purified wild type chromosomal DNA (Lane 4) and plasmid pYUB669 containing the ΔlysA5:res-aph-res allele (Lane 3). Also shown is a schematic of the primers positioned on lysA+ and ΔlysA5:res-aph-res.
Figure 3:
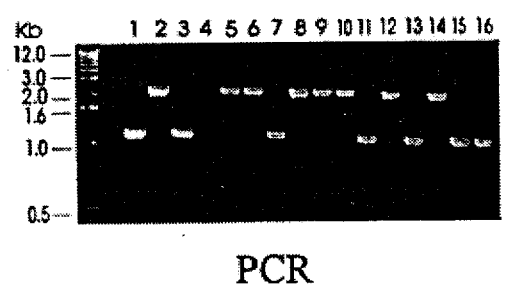
Figure 3:
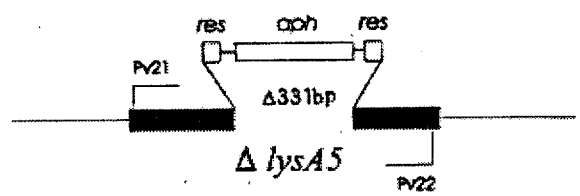
Figure 4:
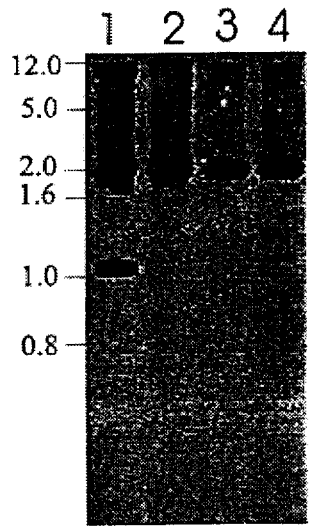
FIG. 4 illustrates Southern blot analysis of the lysA and leuCD locus of M. bovis BCG Pasteur, Copenhagen and Moreau auxotrophic mutants. Genomic DNA from the auxotroph strains was digested with ApaLI for ΔlysA5:res-aph-res auxotrophs or SacII for Δ leuCD6:res-aph-res auxotrophs. Panel A depicts genomic DNA from wild type BCG sub-strain Pasteur (Lane 1), BCG substrain Pasteur auxotroph $mc^2$1507 (Lane 2), BCG substrain Copenhagen $mc^2$1508 (Lane 3) and BCG substrain Moreau $mc^2$1509 (Lane 4), probed with lysA PCR product from BCG Pasteur wild type genomic DNA. The wild type fragment is the expected 1.1 bp while the genomic DNA from the auxotrophic strains has the expected 2.2 kb fragment. Panel B depicts genomic DNA from wild type BCG sub-strain Pasteur (Lane 1), BCG substrain Pasteur auxotroph $mc^2$1510 (Lane 2), BCG substrain Copenhagen $mc^2$1511 (Lane 3) and BCG substrain Moreau $mc^2$1512 (Lane 4), probed with 3.3 kb PstI-HindIII fragment from pYUB853. The wild type fragment is the expected 1.9 kb while the genomic DNA from the auxotrophic strains has the expected 3.4 kb fragment. Also shown is the schematic of the marked deletion alleles of ΔlysA5:res-aph-res and ΔleuCD6:res-aph-res.
Figure 4:
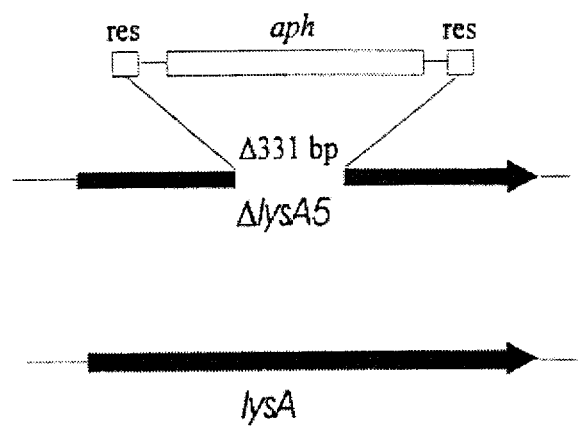
Figure 4:
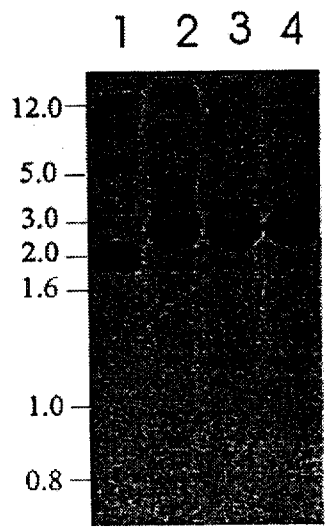
Figure 4:
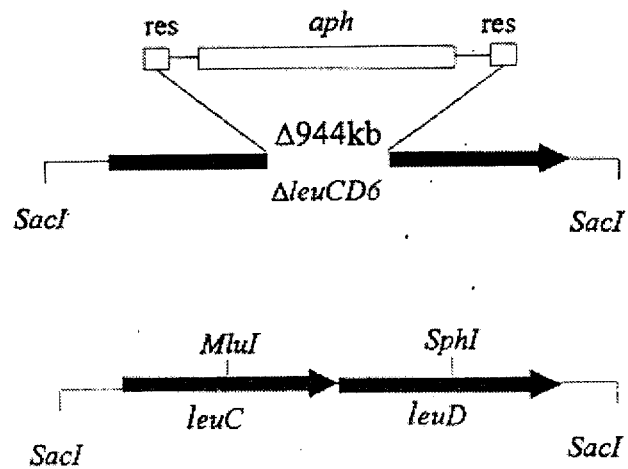

Construction of lysA auxotrophic mutants of three different BCG strains by specialized transduction: To test if the conditionally replicating mycobacteriophages could be used as specialized transducing phages in slow growing mycobacteria, the inventors generated lysine auxotrophs in BCG using an aph-marked deletion allele of the lysA gene (ΔlysA5:res-aph-res). A screen for lysine auxotrophy would allow one to readily distinguish allelic exchange events from spontaneous $Kan^R$ mutants or illegitimate recombination events. Moreover, since the BCG sub-strains represent related, but genetically distinct variants, this system would allow one to test the ability of specialized transducing phages to engineer mutations in various mutant backgrounds. A DNA fragment containing the *M. tuberculosis* ΔlysA4:res-aph-res allele flanked by approximately 1 kb of DNA on each side in the cosmid pYUB598 was engineered into the conditionally replicating phage phAE87. High titers of the resulting phage, phAE128, were generated using *M. smegmatis*. Three different strains of BCG, Pasteur, Copenhagen and Moreau, were infected with phAE128 with a MOI of 10. Since the time required for optimal recombination was unknown, cell-phage mixtures were incubated at 37° C. for different time intervals before plating on complete medium containing kanamycin (Table 4). $Kan^R$ colonies were obtained at frequencies of approximately $10^{-6}$ of input cells for all three BCG strains at all three incubation times. Cell titers performed at the start of infection and 24 h later revealed no significant change in cell numbers (data not shown). To test for allelic exchange events, the $Kan^R$ transductants were screened for lysine auxotrophy (FIG. 3, Panel A). While the numbers of $Kan^R$ colonies did not increase significantly during the varied incubation times, a slight increase in the percentage of lysine auxotrophs was observed in all three BCG strains. The highest percentage of auxotrophs was observed in BCG-Pasteur and BCG-Copenhagen after 24 h outgrowth time (34% and 29% respectively) where the number of auxotrophs nearly tripled. Although unexpectedly low frequency of allelic exchange was observed when using BCG-Moreau strain this tendency of increase in the number of auxotrophs after 24 h outgrowth time (from 2% to 6%) was also observed. To test if the lysine auxotrophy resulted from an allelic exchange of the ΔlysA5:res-aph-res allele into the BCG chromosomes, a PCR analysis of the lysA locus was performed. For all the auxotrophs examined (>10 for each strain), the PCR analysis yielded only a single band of 2.4 kb, the expected size for the ΔlysA5:res-aph-res allele. In contrast, $Kan^R$ prototrophic colonies yielded a single band of 1.1 kb, consistent with the size of the wild type $lysA^+$ allele of the parent strains (see FIG. 3, Panel B for representative data for BCG Pasteur). The PCR results were confirmed by Southern blot analysis (FIG. 4, Panel A). For all three BCG strains, the lysine auxotrophs had a single hybridization band of the same size as the ΔlysA5:res-aph-res allele. In contrast, the parent strains or the $Kan^R$ prototrophic strains had a single band that corresponded to the wild-type $lysA^+$ allele.

Construction of ΔleuCD auxotrophic mutants of three different BCG strains by specialized transduction: To test the generality of the specialized transduction as a method for insertional inactivation of different genes in slow-growing mycobacteria, the inventors constructed a specialized transducing phage carrying a ΔleuCD6:res-aph-res allele. This allele was inserted into phAE87 to generate the specialized transducing phage phAE134. BCG strains Pasteur, Copenhagen, and Moreau were transduced with phAE134 as described above using a 24-h outgrowth time. Examination of the plates at three weeks of incubation revealed the presence of both large and small colonies. None of the large colonies of each BCG strain were auxotrophic mutants. PCR analysis of 20 large clones revealed the wild-type leuCD alleles (data not shown). Upon further incubation for 2 weeks the small colonies increased in size and then were screened for auxotrophy. A large percentage of the small $Kan^R$ colonies from each BCG sub-strain were leucine auxotrophs (Table 5). Southern analysis confirmed that the leucine auxotrophs had resulted from an allelic exchange of the ΔleuCD6:res-aph-res allele with the wild-type leuCD allele (FIG. 4, Panel B).

C) Discussion

With the availability of the genomic sequence of *M. tuberculosis*, the complete set of genes has been predicted. While precise functions have been assigned to 40% of the predicted genes, 44% have suggested homologies and 16% have no known functions. The determination of the function of an individual gene requires the comparison of the phenotypes of isogenic strains that are genetically identical except for the gene in question. While efficient transposon mutagenesis systems have been developed for *M. tuberculosis* gene replacement has continued to be a difficult and/or time-inefficient process for the slow-growing mycobacteria, particularly in *M. tuberculosis* and *M. bovis*. Accordingly, the inventors describe herein a one-step, time-efficient system for generating gene replacements in mycobacteria using specialized transducing phages. Transduction, a natural system for the exchange of genetic information using phage-mediated gene transfer, was first described as a surprising result following attempts to observe conjugation in Salmonella (36). Unlike conjugation in *E. coli*, it was found that genetic material could be transferred by a nuclease resistant mechanism that did not require cell-to-cell contact. Upon observing that the gene transfer "agents" passed through filters and were inhibited by antibodies to phage P22, Zinder and Lederberg concluded that a novel phage-mediated gene transfer system had been discovered which was labeled as transduction (36). Similarly, Lenox discovered that phage P1 could mediate gene transfer between *E. coli* strains for a wide variety of genes (15). Later studies revealed that bacteriophage lambda lysates induced from lysogens could mediate the transfer of two genetic markers, gal and bio, that happened to be adjacent to the lambda attachment site, attB (18). This transfer was labeled specialized transduction because it was limited to a few genes, in contrast to generalized transduction of P22 and P1 which could transfer a large number of genetic markers. The basis for specialized transfer is an aberrant excision of the lysogenic phage in contrast to a random "headfull" packaging of chromosomal DNA by the generalized transducing phages. The term "specialized transduction" then refers to the transfer of genetic material with a hybrid phage molecule, that is part phage and part chromosomal DNA. In contrast, generalized transduction is mediated by a sub-population of phages in a lysate that contain entirely chromosomal DNA (35). Specialized transducing phages can transfer a specific set of genes in an individual lysate, whereas generalized transducing phages can transfer a variety of genes within a single lysate.

Conditionally replicating mycobacteriophages have proven to be a highly efficient genetic system for generating large libraries of independent transposon mutants both in BCG and *M. tuberculosis* since they provide the means to deliver transposon constructs to virtually every cell in the bacterial population (12) (10) (3) (19). The inventors have modified this system and have generated specialized transducing mycobacteriophages which are able to deliver homologous DNA substrate for allelic exchanges. Thus, these phages share some of the properties of both specialized and generalized transducing phages. They resemble the specialized transducing phages by having only a small, non-essential part of the phage genome replaced with chromosomal DNA, while the allelic exchange which they promote by homologous recombination via double cross-over resembles more the P1 or P22 generalized transducing phages. One of the big advantages of the specialized transducing mycobacteriophages used in this study is the presence of natural counter-selection mechanism for the integration of the whole phage or parts of it into the host chromosome via single cross-over or illegitimate recombination since if such integration occurs an expression of the phage genes as a part of the chromosome will be deleterious for the host cell. In numerous hybridization experiments using phage DNA sequences as a probe the inventors were never able to find phage integration into the hist chromosome of the auxotrophic strains (data not shown). The inventors have demonstrated the reproducibility and the utility of the specialized transduction for the delivery of homologous DNA substrates for allelic exchanges of marked mutations in both fast- and slow growing mycobacteria. Using *M. tuberculosis* sequence data base (7), ΔlysA5:res-aph-res deletion mutant alleles were generated which when introduced via transduction into three different sub-strains of BCG generated lysine auxotrophs with a frequency which greatly exceeds the frequencies obtained when using a "suicide" plasmid approach or long linear DNA substrates. This difference could be explained with the very high efficiency of delivery of the recombination substrate into the host cell in comparison with the transformation efficiency via electroporation. When using the specialized transducing phages at a proper multiplicity of infection virtually every cell in the bacterial population is infected by the recombinant phage. Such results are in agreement with the conclusions made by Pavelka et al. (21) that the frequency of the homologous recombination in the slow growing mycobacteria does not differ drastically from that observed in the fast growing mycobacteria, although, the fact that the same target gene was used does not waive the concern that the lysA region of the chromosome is more permissive for homologous recombination.

This novel method of specialized transduction for mycobacteria has several useful features. First, the specialized transduction phage system can be readily generalized to any set of genes by virtue of the facile cloning properties of the shuttle phasmid properties of the conditionally-replicating mycobacteriophage vector. Once a specific mutated allele is engineered into the phage, the phage allows for introduction of that mutated allele in any BCG strain or BCG mutant. The inventors have incorporated chromosomal DNA fragments of at least 4 kb containing several particular genes. It is anticipated that the cloning capacity of the phasmid vector can be expanded up to 8 kb by generating additional deletions in nonessential regions of the phage genome. This improvement of the system would allow linkage analyses to be performed for characterizing specific point mutations in a particular gene that has a linked selectable marker next to it. In contrast to a plasmid transformation system, the present invention is a single step system for obtaining independent allelic exchanges. Using plasmid transformation systems makes it difficult to distinguish independent homologous recombination events from the siblings. Ultimately, the present invention should prove to be very useful for the construction and development of *M. tuberculosis*-based vaccine strains with numerous defined non-revertible mutations.

TABLE 1

Bacterial strains

| Bacteria | Description | Reference or source |
|---|---|---|
| *E. coli* K-12 strains | | |
| DH5α | F−[φ80ΔlacZM15] Δ(lacZYA-argF) galU169 deoR recA1 endA1 hsdR17 glnV44 thi-1 gyr A96 relA1 | (9) |
| HB101 | F−Δ(gpt-proA)62 leuB1, gln V44 ara14 galK2 lacY1 hsd20 rpsl20 xyl-5 mtl-1 | (6) |
| BCG strains: | | |
| Pasteur | vaccine strain | Statens Seruminstitut |
| mc²1507 | BCG(Pasteur) ΔlysA5::res-aph-res | This work |
| mc²1510 | BCG(Pasteur) ΔleuCD6::res-aph-res | This work |
| Copenhagen | vaccine strain | Statens Seruminstitut |
| mc²1508 | BCG(Copenhagen) ΔlysA5::res-aph-res | This work |
| mc²1511 | BCG(Copenhagen) ΔleuCD6::res-aph-res | This work |
| Moreau | vaccine strain | Statens Seruminstitut |
| mc²1509 | BCG(Moreau) ΔlysA5::res-aph-res | This work |
| mc²1512 | BCG(Moreau) ΔleuCD6::res-aph-res | This work |

TABLE 1-continued

Bacterial strains

| Bacteria | Description | Reference or source |
|---|---|---|
| *M. smegmatis* strains | | |
| mc²155 | ept-1 | (31) |
| mc²1494 | mc²155 ΔlysA4::res-hyg-res | This work |

TABLE 2

Shuttle phasmids, plasmids and cosmids

| | Description | Reference |
|---|---|---|
| Shuttle phasmids | | |
| phAE87 | PH101::pYUB328 fails to replicate at 37° C. | (7) |
| phAE128 | phAE87::pYUB586 | This work |
| phAE134 | phAE87::pYUB597 | This work |
| phAE143 | phAE87::pYUB854 | This work |
| phAE144 | phAE87::pYUB855 | This work |
| Plasmids | | |
| pBluescript KSII+ | ColE1 based phagemid (ori fl+) KpnI-SacI | Stratagene |
| pYUB619 | pMV261 (argS+ΔlysA4::res-hyg-res) | (19) |
| pYUB665 | pBluescript KSI+::argS+ ΔlysA5::res-aph-res hsd+ thrC+ thrB+ | This work |
| pYUB853 | pBluescript KS II leuC leuD | (19) |
| pYUB854 | pBluescript KS II::(Δ leuCD6::res-aph-res) | This work |
| Cosmids | | |
| pYUB328 | ColE1 amp^R PacI excisable double λ-cos vector | (2) |
| pYUB552 | 2.4 kb derivative of pYUB328 | (3) |
| pYUB572 | 2.1 kb derivative of pYUB552 | This work |
| pYUB586 | pYUB572::(argS Δ lysA5::res-aph-res hsd) | This work |
| pYUB597 | pYUB572::(Δ leuCD6::res-aph-res) | This work |
| pYUB854 | pYUB572::(arg Δ lysA4::res-hyg-res hsd) orientation 1 | This work |
| pYUB855 | pYUB572::(arg Δ lysA4::res-hyg-res hsd) orientation 2 | This work |

TABLE 3

Auxotroph analysis of *M. smegmatis* mc²155 Hyg^R colonies following transduction with phAE143 and phAE144

| | | phAE143 | | | phAE144 | |
|---|---|---|---|---|---|---|
| Outgrowth time | Transduction frequency | # Lys−/ # Hyg | % allelic exchange | Transduction frequency | # Lys−/ # HygR | % allelic exchange |
| 0 hours | 6.5 × 10⁻⁶ | 90/96 | 94 | 5.8 × 10⁻⁶ | 87/96 | 90 |
| 2 hours | 8.7 × 10⁻⁶ | 93/96 | 97 | 7.6 × 10⁻⁶ | 91/96 | 95 |

TABLE 4

Auxotroph analysis of CG Kan$^R$ colonies following phAE128 transduction at different outgrowth time intervals

| Out-growth time | Pasteur | | Copenhagen | | Moreau | |
|---|---|---|---|---|---|---|
| | Lys$^-$/Kan$^R$ | % allelic exchange | Lys$^-$/Kan$^R$ | % allelic exchange | Lys$^-$/Kan$^R$ | % allelic exchange |
| 6 hours | 34/286 | 12 | 10/146 | 7 | 2/128 | 2 |
| 12 hours | 104/372 | 28 | 37/289 | 13 | 0/146 | 0 |
| 24 hours | 168/495 | 34 | 125/432 | 29 | 13/230 | 6 |

TABLE 5

Auxotroph analysis of BCG KanR colonies following transduction with phAE134

| | Large Kan$^R$ colonies | | | Small Kan$^R$ colonies | | |
|---|---|---|---|---|---|---|
| BCG strain | Transduction frequency | Leu-/KanR | % allelic exchange | Transduction frequency | Leu-/KanR | % allelic exchange |
| Pasteur | 7.8 × 10$^{-6}$ | 0/96 | 0 | 1.9 × 10$^{-5}$ | 60/96 | 62 |
| Copenhagen | 1.5 × 10$^{-6}$ | 0/96 | 0 | 3.5 × 10$^{-6}$ | 46/96 | 48 |
| Moreau | 1.9 × 10$^{-6}$ | 0/96 | 0 | 3.6 × 10$^{-6}$ | 95/96 | 97 |

REFERENCES

1. Azad, A. K., T. D. Sirakova, L. M. Rogers, and P. E. Kolattukudy. 1996. Targeted replacement of the mycocerosic acid synthase gene in Mycobacterium bovis BCG produces a mutant that lacks mycosides. Proc. Natl Acad. Sci. U.S.A. 93(10) :4787–92.

2. Balasubramanian, V., M. S. Pavelka, Jr., S. S. Bardarov, J. Martin, T. R. Weisbrod, R. A. McAdam, B. R. Bloom, and W. R. Jacobs, Jr. 1996. Allelic exchange in Mycobacterium tuberculosis with long linear recombination substrates. J Bacteriol. 178(1):273–9.

3. Bardarov, S., J. Kriakov, C. Carriere, S. Yu, C. Vaamonde, R. A. McAdam, B. R. Bloom, G. F. Hatfull, and W. R. Jacobs, Jr. 1997. Conditionally replicating mycobacteriophages: a system for transposon delivery to Mycobacterium tuberculosis. Proc Natl Acad Sci U.S.A. 94(20):10961–6.

4. Berg, C. M., N. B. Vartak, G. Wang, X. Xu, L. Liu, D. J. MacNeil, K. M. Gewain, L. A. Wiater, and D. E. Berg. 1992. The m gamma delta-1 element, a small gamma delta (Tn1000) derivative useful for plasmid mutagenesis, allele replacement and DNA sequencing. Gene. 113(1):9–16.

5. Berthet, F. X., M. Lagranderie, P. Gounon, C. Laurent-Winter, D. Ensergueix, P. Chavarot, F. Thouron, E. Maranghi, V. Pelicic, D. Portnoi, G. Marchal, and B. Gicquel. 1998. Attenuation of virulence by disruption of the Mycobacterium tuberculosis erp gene. Science. 282(5389):759–62.

6. Carriere, C., P. F. Riska, O. Zimhony, J. Kriakov, S. Bardarov, J. Burns, J. Chan, and W. R. Jacobs, Jr. 1997. Conditionally replicating luciferase reporter phages: improved sensitivity for rapid detection and assessment of drug susceptibility of Mycobacterium tuberculosis. J Clin Microbiol. 35(12):3232–9.

7. Cole, S. T., R. Brosch, J. Parkhill, T. Garnier, C. Churcher, D. Harris, S. V. Gordon, K. Eiglmeier, S. Gas, C. E. Barry, 3rd, F. Tekaia, K. Badcock, D. Basham, D. Brown, T. Chillingworth, R. Connor, R. Davies, K. Devlin, T. Feltwell, S. Gentles, N. Hamlin, S. Holroyd, T. Hornsby, K. Jagels, B. G. Barrell, et al. 1998. Deciphering the biology of Mycobacterium tuberculosis from the complete genome sequence [comments] [published erratum appears in Nature Nov. 12, 1998;396(6707):190]. Nature. 393(6685) :537–44.

8. Ford, M. E., Stenstrom, C, Hendrix, R. W., Hatfull, G. F. 1999. Mycobacteriophage TM4: Genome structure and gene expression. unpublished.

9. Hatfull, G. F., J. J. Salvo, E. E. Falvey, V. Rimphanitchayakit, and N. D. Grindley. 1988. Site-specific recombination by the gamma-delta resolvase. Cambridge University Press.

10. Jacobs, W. R., Jr., R. G. Barletta, R. Udani, J. Chan, G. Kalkut, G. Sosne, T. Kieser, G. J. Sarkis, G. F. Hatfull, and B. R. Bloom. 1993. Rapid assessment of drug susceptibilities of Mycobacterium tuberculosis by means of luciferase reporter phages [comments]. Science. 260(5109) :819–22.

11. Jacobs, W. R., Jr., G. V. Kalpana, J. D. Cirillo, L. Pascopella, S. B. Snapper, R. A. Udani, W. Jones, R. G. Barletta, and B. R. Bloom. 1991. Genetic systems for mycobacteria. Methods Enzymol. 204:537–55.

12. Jacobs, W. R., Jr., M. Tuckman, and B. R. Bloom. 1987. Introduction of foreign DNA into mycobacteria using a shuttle phasmid. Nature. 327(6122):532–5.

13. Kalpana, G. V., B. R. Bloom, and W. R. Jacobs, Jr. 1991. Insertional mutagenesis and illegitimate recombination in mycobacteria. Proc. Natl Acad. Sci. U.S.A. 88(12):5433–7.

14. Knipfer, N., A. Seth, and T. E. Shrader. 1997. Unmarked gene integration into the chromosome of Mycobacterium smegmatis via precise replacement of the pyrF gene. Plasmid. 37(2):129–40.

15. Lenox, E. S. 1955. Transduction of linked genetic characters of the host by bacteriophage P1. Virology. 1:190–206.

16. McFadden, J. 1996. Recombination in mycobacteria. Mol Microbiol. 21(2):205–11.

17. Mizuguchi, Y., K. Suga, and T. Tokunaga. 1976. Multiple mating types of Mycobacterium smegmatis. Jpn J Microbiol. 20(5) :435–43.

18. Morse, M. L., E. M. Lederberg, and J. Lederberg. 1956. Transduction in Eschericha coli K-12. Genetics. 41:142–156.

19. Murphy, K. C. 1998. Use of bacteriophage lambda recombination functions to promote gene replacement in Escherichia coli. J Bacteriol. 180(8):2063–71.

20. Parsons, L. M., C. S. Jankowski, and K. M. Derbyshire. 1998. Conjugal transfer of chromosomal DNA in Mycobacterium smegmatis. Mol Microbiol. 28(3) :571–82.

21. Pavelka, M. S., Jr. Jacobs, W. R., Jr. 1999. A Comparison of the construction of unmarked deletion mutations in Mycobacterium smegmatis, M. bovis bacille Calmette-Guerin (BCG) and M. tuberculosis H37Rv by allelic exchange. unpublished.

22. Pavelka, M. S., Jr., and W. R. Jacobs, Jr. 1996. Biosynthesis of diaminopimelate, the precursor of lysine and a component of peptidoglycan, is an essential function of Mycobacterium smegmatis. J Bacteriol. 178(22) :6496–507.

23. Pelicic, V., M. Jackson, J. M. Reyrat, W. R. Jacobs, Jr., B. Gicquel, and C. Guilhot. 1997. Efficient allelic exchange and transposon mutagenesis in *Mycobacterium tuberculosis*. *Proc. Natl Acad. Sci. U.S.A.* 94(20):10955–60.

24. Pelicic, V., J. M. Reyrat, and B. Gicquel. 1996. Generation of unmarked directed mutations in mycobacteria, using sucrose counter-selectable suicide vectors. *Mol Microbiol.* 20(5):919–25.

25. Pelicic, V., J. M. Reyrat, and B. Gicquel. 1996. Positive selection of allelic exchange mutants in *Mycobacterium bovis* BCG. *FEMS Microbiol Lett.* 144(2–3):161–6.

26. Raj, C. V., and T. Ramakrishnan. 1970. Transduction in *Mycobacterium smegmatis*. *Nature.* 228(268):280–1.

27. Reed, R. R. 1981. Resolution of cointegrates between transposons gamma delta and Tn3 defines the recombination site. *Proc. Natl Acad. Sci. U.S.A.* 78(6):3428–32.

28. Reyrat, J. M., F. X. Berthet, and B. Gicquel. 1995. The urease locus of *Mycobacterium tuberculosis* and its utilization for the demonstration of allelic exchange in *Mycobacterium bovis* bacillus Calmette-Guerin. *Proc. Natl Acad. Sci. U.S.A.* 92(19):8768–72.

29. Riska, P. F., Y. Su, S. Bardarov, L. Freundlich, G. Sarkis, G. Hatfull, C. Carriere, V. Kumar, J. Chan, and W. R. Jacobs, Jr. 1999. Rapid film-based determination of antibiotic susceptibilities of *Mycobacterium tuberculosis* strains by using a luciferase reporter phage and the Bronx Box. *J Clin Microbiol.* 37(4):1144–9.

30. Sambrook, J., E. F. Fritsch, and T. Maniatis. 1989. *Molecular cloning: A Laboratory Manual,* 2 ed. Cold Spring Harbor Lab. Press, Plainview, N.Y.

31. Sander, P., A. Meier, and E. C. Bottger. 1995. rpsL+: a dominant selectable marker for gene replacement in mycobacteria. *Mol Microbiol.* 16(5):991–1000.

32. Snapper, S. B., L. Lugosi, A. Jekkel, R. E. Melton, T. Kieser, B. R. Bloom, and W. R. Jacobs, Jr. 1988. Lysogeny and transformation in mycobacteria: stable expression of foreign genes. *Proc. Natl Acad. Sci. U.S.A.* 85(18):6987–91.

33. Tokunaga, T., Y. Mizuguchi, and K. Suga. 1973. Genetic recombination in mycobacteria. *J Bacteriol.* 113(3):1104–11.

34. Wards, B. J., and D. M. Collins. 1996. Electroporation at elevated temperatures substantially improves transformation efficiency of slow-growing mycobacteria. *FEMS Microbiol Lett.* 145(1):101–5.

35. Weisberg, R. A. 1996. Specialized transduction, p. 2442–2448. In F. C. e. a. n. e. Neidhardt (ed.), *Escherichia coli* and Salmonella: cellular and molecular biology, 2 ed, vol. 2. ASM Press, New York.

36. Zinder, N., and J. Lederberg. 1952. Genetic exchange in Salmonella. *J. Bacteriol.* 64:679–699.

37. Murray C., et al. 1997, p. 273 in Global Burden of Diseases. Harvard Univ. Press, Cambridge, Mass.

All publications mentioned herein are incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for producing a recombinant mutant slow-growing mycobacterium, comprising: (a) infecting a slow-growing mycobacterium with a conditional transducing phage comprising a conditional mycobacteriophage containing an *E. coli* bacteriophage lambda cosmid inserted into a non-essential region of the mycobacteriophage, said cosmid comprising a mutated DNA substrate which is homologous to a wildtype nucleic acid sequence of a slow-growing mycobacterium; and (b) culturing the infected slow-growing mycobacterium under conditions wherein the conditional transducing phage does not replicate and the mutated DNA substrate is incorporated into the chromosome of the slow-growing mycobacterium by homologous recombination, thereby generating the recombinant mutant slow-growing mycobacterium.

2. The method of claim 1, wherein the wildtype nucleic acid sequence of the slow-growing mycobacterium encodes a protein or a polypeptide.

3. The method of claim 2, wherein the protein or polypeptide is an enzyme essential in the biosynthetic pathway of a nutrient, structural component or an amino acid.

4. The method of claim 3, wherein the wildtype nucleic acid sequence encodes lysA or leuCD.

5. The method of claim 4, wherein the resulting recombinant mutant slow-growing mycobacterium is auxotrophic for lysine or leucine.

6. The method of claim 5, wherein the slow-growing mycobacterium is obtained from a mycobacterial strain selected from the group consisting of *M. tuberculosis, M. bovis-BCG* and *M. leprae*.

7. The method of claim 1, wherein the slow-growing mycobacterium is *M. tuberculosis*.

8. The method of claim 1, wherein the slow-growing mycobacterium is *M. bovis-BCG*.

9. The method of claim 2, wherein the slow-growing mycobacterium is *M. tuberculosis*.

10. The method of claim 2, wherein the slow-growing mycobacterium is *M. tuberculosis*.

11. The method of claim 3, wherein the slow-growing mycobacterium is *M. tuberculosis*.

12. The method of claim 3, wherein the slow-growing mycobacterium is *M. bovis-BCG*.

13. The method of claim 4, wherein the slow-growing mycobacterium is *M. tuberculosis*.

14. The method of claim 15, wherein the slow-growing mycobacterium is *M. bovis-BCG*.

15. The method of claim 1, wherein the slow-growing mycobacterium is *M. tuberculosis*, the wildtype nucleic acid sequence encodes lysA, and the resulting recombinant mutant slow-growing mycobacterium is auxotrophic for lysine.

16. The method of claim 1, wherein the slow-growing mycobacterium is *M. bovis-BCG*, the wildtype nucleic acid sequence encodes lysA, and the resulting recombinant mutant slow-growing nycobacterium is auxotrophic for lysine.

17. The method of claim 1, wherein the slow-growing mycobacterium is *M. tuberculosis*, the wildtype nucleic acid sequence encodes leuCD, and the resulting recombinant mutant slow-growing mycobacterium is auxotrophic for leucine.

18. The method of claim 1, wherein the slow-growing mycobacterium is *M. bovis*-BCG, the wild type nucleic acid sequence encodes leuCD, and the resulting recombinant mutant slow-growing mycobacterium is auxotrophic for leucine.

* * * * *

```
                              SEQUENCE LISTING

<160> NUMBER OF SEQ ID NOS: 6

<210> SEQ ID NO: 1
<211> LENGTH: 20
<212> TYPE: DNA
<213> ORGANISM: Mycobacterium sp.

<400> SEQUENCE: 1
tgaacaccgc ctttggcaat                                                    20

<210> SEQ ID NO: 2
<211> LENGTH: 20
<212> TYPE: DNA
<213> ORGANISM: Mycobacterium sp.

<400> SEQUENCE: 2
gccttacgca ccgatgcctt                                                    20

<210> SEQ ID NO: 3
<211> LENGTH: 20
<212> TYPE: DNA
<213> ORGANISM: Mycobacterium sp.

<400> SEQUENCE: 3
gaattccact gacgcagctc                                                    20

<210> SEQ ID NO: 4
<211> LENGTH: 20
<212> TYPE: DNA
<213> ORGANISM: Mycobacterium sp.

<400> SEQUENCE: 4
```

-continued

```
gccgaccatg ttgtaacgac                                                  20

<210> SEQ ID NO: 5
<211> LENGTH: 18
<212> TYPE: DNA
<213> ORGANISM: Mycobacterium sp.

<400> SEQUENCE: 5
aaggccggat gacgatct                                                    18

<210> SEQ ID NO: 6
<211> LENGTH: 20
<212> TYPE: DNA
<213> ORGANISM: Mycobacterium sp.

<400> SEQUENCE: 6
tcttgaacgg cagcaccact                                                  20
```